| United States Patent [19] | [11] Patent Number: 4,826,761 |
| Arai et al. | [45] Date of Patent: May 2, 1989 |

[54] MULTILAYER ANALYTICAL ELEMENT FOR ANALYSIS OF CHOLESTEROL

[75] Inventors: Fuminori Arai; Takeshi Igarashi, both of Saitama, Japan

[73] Assignee: Fuji Photo Film Co, Ltd., Kanagawa, Japan

[21] Appl. No.: 883,065

[22] Filed: Jul. 8, 1986

[30] Foreign Application Priority Data

Jul. 9, 1985 [JP] Japan .................... 60-150567

[51] Int. Cl.$^4$ .............................................. C12Q 1/60
[52] U.S. Cl. ..................................... 435/11; 435/19; 435/25; 435/28
[58] Field of Search ................... 435/11, 19, 25, 28

[56] References Cited

U.S. PATENT DOCUMENTS

| 3,983,005 | 9/1976 | Goodhue et al. ................ 435/11 |
| 3,992,158 | 11/1976 | Przybylowicz et al. .......... 435/11 |
| 4,089,747 | 5/1978 | Jungfleisch ...................... 435/11 |
| 4,291,121 | 9/1981 | Acquati et al. . | |
| 4,414,326 | 11/1983 | Goldberg ......................... 435/11 |

*Primary Examiner*—Sam Rosen
*Attorney, Agent, or Firm*—Jules E. Goldberg

[57] ABSTRACT

An integral multilayer analytical element for analysis of cholesterol which comprises a water-impermeable light-transmissive support, a hydrophilic layer and a spreading layer superposed in this order, and contains cholesterol esterase, cholesterol oxidase, peroxidase and a coloring reagent composition, which is characterized, in that the above coloring reagent composition is a combination of 4-aminoantipyrine or its derivative and 2-hydroxy-3,5-dichlorobenzene sulfonic acid, and in that pH of the layer where coloring reaction proceeds is kept in the range of 7.5 to 9.

This analytical element is stable, and capable of preserving more than 8 months without fogging.

5 Claims, No Drawings

MULTILAYER ANALYTICAL ELEMENT FOR ANALYSIS OF CHOLESTEROL

BACKGROUND OF THE INVENTION

1. Field of the Invention

This invention relates to an improvement of a dry-type integral multilayer analytical element for analysis of cholesterol contained in an aqueous liquid sample such as blood and other body fluids.

2. Description of Prior Art

Recently, as a dry-type analytical element, integral multilayer analytical elements wherein a water-absorptive reagent layer containing reagents for color-forming reaction and a hydrophilic polymer binder and a porous spreading layer are provided on a light-transmissive support have bean developed. Various samples can be analyzed by using this multilayer analytical element where the reagents are changed, and the multilayer analytical elements for analysis of cholesterol have also been known (Clin. Chem., 28(5), 1159–1162 (1982) and U.S. Pat. No. 4,012,325).

Such a conventional multilayer analytical element for analysis of cholesterol consisted of a light-transmissive support, a gelatin layer and a spreading layer laminated in this order, and necessary reagents such as cholesterol esterase, cholesterol oxidase, peroxidase, a leuco pigment, etc. were added as illustrated in the following (CLIN. CHEM., 28(5), 1159–1162 (1982)). The pH of the gelatin layer was adjusted to 6.25.

| | |
|---|---|
| Spreading Layer | BaSO$_4$ |
| | Cellulose Acetate |
| | Octylphenoxypolyethoxyethanol |
| | (Hydroxyethylene Units; 9–10) |
| | KH$_2$PO$_4$ |
| | Cholesterol esterase |
| | Cholesterol oxidase |
| | Peroxidase |
| | Triarylimidazol leuco pigment |
| Gelatin Layer | Gelatin (pH 6.25) |
| Support | Transparent polyethylene terephthalate film |

In the case of the conventional multilayer analytical element for analysis of cholesterol, the leuco pigment gradually colors during preservation, and therefore, its stability for preservation is inferior. Since this coloration is accelerated in the open air, the analytical element should be used in a short period after opening.

SUMMARY OF THE INVENTION

It is an object of the invention to provide a multilayer analytical element for the analysis of cholesterol capable of having long term stability without coloration.

The present inventors have investigated in order to solve this problem, and found that the coloration during preservation can be avoided by using a combination of 4-aminoantipyrine or its derivative and 2-hydroxy-3,5-dichlorobenzene sulfonic acid. However, the coloring rate is slow. Then, they have further investigated, and they have found that when pH is adjusted to 7.5 to 9.0, the coloring rate is raised to the level of the convetional leuco pigment.

Thus, the integral multilayer analytical element for analysis of cholesterol of the present invention comprises a water-impermeable light-transmissive support, a hydrophilic layer containing a hydrophilic polymer binder and a spreading layer superposed in this order, and contains cholesterol esterase, cholesterol oxidase, peroxidase and a coloring reagent composition, which is characterized, in that the above coloring reagent composition is a combination of 4-aminonantipyrine, its acid adduct salt, its derivative or its acid adduct salt and 2-hydroxy-3,5-dichlorobenzene sulfonic acid or a salt thereof, and in that the pH of the layer where coloring reaction proceeds is kept in the range of 7.5 to 9.

DETAILED DESCRIPTION OF THE INVENTION

As the water-impermeable light-transmissive support, a known support employed in an usual multilayer analytical element may be employed. Such a support is a sheet or a laminate having a thickness in the range from about 50 $\mu$m to about 1 mm, preferably from about 80 $\mu$m to about 0.3 mm and being clear in the range from near-ultraviolet to near infrared regions. Such a sheet or a laminate may be made from a polyester (for example, polyethylene terephthalate or polycarbonateor bisphenol A), a cellulose ester (for example, cellulose diacetate, cellulose triacetate or cellulose acetate propionate), or polystyrene. A known undercoating layer or a known adhesive layer, such as, disclosed in the foregoing patent specifications may be provided on the surface of the support in order to secure the adhesion of the support to the hydrophilic layer, etc.

The hydrophilic layer is the layer to accumulate the colored material produced by the oxidizing coupling reaction of 4-aminoantipyrine or its derivative and 2-hydroxy-3,5-diclorobenzene sulfonic acid, and consists of a hydrophilic polymer binder alone or together with other components. The hydrophilic layer may also function as a water absorption layer which absorbs water to swell and which receives and accumulates the colored material, and as a registration layer which contains a mordant having negative charge or positive charge capable of immobilizing the colored material and which absorbs water to swell. The swelling ratio on 30° C. at water absorption of the hydrophilic polymer binder is in the range from about 150% to about 2000%, preferably about 250% to about 1500%. Examples of the hydrophilic polymer binder usable for the hydrophilic layer are gelatin including acid treated gelatin and deionized gelatin, gelatin delivatives such as phthalated gelatin and hydroxyalkyl acrylate grafted gelatin, agarose, pullulan, pullulan derivatives, polyacrylamide, polyvinyl alcohol and polyvinyl pyrrolidione. They are disclosed in EP No. 0,119,861 A and EP No. 0,142,849 A. The thickness of the hydrophilic layer in the dry state is usually about 1 $\mu$m to about 100 $\mu$m, preferably about 3 $\mu$m to about 50 $\mu$m, and particularly preferable about 5 $\mu$m to about 30 $\mu$m. This hydrophilic layer may contain a part of or all of the reagents such as, the enzymes, 4-aminoantipyrine, etc., a base polymer. An acid polymer, a mordant, etc., known to the art may also be contained in this layer.

The spreading layer spreads a liquid sample. Various non-fibrous isotroically porous spreading layers, such as a memberane filter (blushed polymer layer) disclosed in U.S. Pat. No. 3,992,158, a continuous microspace-containing porous layer where polymer particulates, glass particulates or diatomaceous earth are dispersed in a hydrophilic polymer binder, a continuous microspace-containing porous layer where polymer particulates, glass particulates, etc. are joined so as to contact each other at a point by using a polymer adhesive which does not swell in water (one having a three-dimensional lattice structure layer) as disclosed in U.S. Pat. No. 4,258,001, and various fibrous porous spreading layers, such as a spreading layer of woven fabric as disclosed in U.S. Pat. No. 4,292,272 a spreading layer of knitted fabric as disclosed in EP No. 0,162,302 A and a spreading layer comprising a paper containing a fibrous pulp of an organic polymer as disclosed in Japanese Patent KOKAI No. 57-148250 may be utilized.

The spreading layer is laminated directly or through an adhesive layer. This spreading layer may contain a part of or all of the reagents, such as, the enzymes, 4-aminoantipyrine, etc.

Various layers disclosed in the specifications of the foregoing patents may be introduced into the multilayer element of the invention. Such layers include a reagent layer, a light-shielding layer, a light-reflecting layer, a filter layer a semipermeable membrane layer, a barrier layer, a diffusion-hindering layer (migration-inhibiting layer) and a layer having two or more of the functions mentioned above.

The reagent layer contains a part of or all of the reagents, such as, the enzymes, 4-aminoantipyrine, etc., and it is non-porous and water-absorptive or microporous and water-permeable.

A hydrophilic polymer binder which is employed for the substantially non-porous and water-absorptive reagent layer functions as a medium for dissolving or dispersing the reagents uniformly. It also functions to absorb the water in a sample and to carry to cholesterol together with the water. The hydrophilic polymer binder may be selected from those illustrated in the foregoing named hydrophilic layer. The thickness of the substantially non-porous reagent layer in dry state is about 3 $\mu$m to about 50 $\mu$m, and preferably about 5 $\mu$m to about 30 $\mu$m. It is preferable that this reagent layer is substantially transparent.

The microporous and water-permeable reagent layer comprises a microporous structure layer constructed by solid particulates and a hydrophilic polymer binder as the binder thereof and reagent(s) or a reagemt composition contained therein. The microporous structure layer referred herein has a continuous microspaces structure composed of microporous or non-porous particulates and a hydrophilic polymer binder joining them.

Examples of the microporous or non-porous particulates, include cellulose particulates, such as, microcrystalline cellulose and cellulose fine powder, particulates of silicon dioxide compound, such as, silica and diatomaceous earth, silicate particulates, such as, zeolite, polymer particulates, glass particulates, and various ceramic particulates. The hydrophilic polymer binder may be selected from the illustrated in the foregoing hydrophilic layer or aqueos latex of copolymer containing more than 2% of hydrophilic repeating unit disclosed in EP No. 0,115,873 A. The thickness of the microporous reagent layer in dry state is about 7 $\mu$m to about 50 $\mu$m, and preferably about 10 $\mu$m to about 30 $\mu$m.

The reagent layer may contain a pH buffer composition, a macromolecular pH buffer, a base polymer, an acid polymer, a macromolecular mordant, etc., known to the art.

A light-shielding layer may be provided on the reagent layer or the hydrophilic layer. The light-shielding layer is water-transmissive or water-permeable, and light-shielding particulates or the particulates having both functions of light-shielding and light-reflecting are dispersed in and held by a small amount of a hydrophilic polymer binder capable of forming a film. The light-shielding layer shields the color of an aqueous liquid sample, particularly the red color of homoglobin in a whole blood sample, spotted on the spreading layer during the measurement of the coloring of the hydrophilic layer which is made by measuring the reflection from the side of the light-transmissive support. This layer may also function as a light-reflecting layer or a background layer.

Examples of the particulates having both functions of light-shielding and light-reflecting are titanium dioxide particulates, such as, rutile, anatase and brookite microcrystalline particulates having a particle size of about 0.1 $\mu$m to about 1.2 $\mu$m, barium sulfate particulates and aluminum particulates and microflakes. Examples of the light-shielding particulates are carbon black, gas black and carbon microbeads. Among them, titanium dioxide particulates and barium sulfate particulates are preferable. The hydrophilic polymer binder having the film-forming property may be selected from the illustrated in the foregoing hydrophilic layer, weakly hydrophilic regenerated cellulose and cellulose acetate. Among them, gelatin, a gelatin derivative and polyacryamide are preferable. To gelatin and a gelatin derivative, a known curing agent (a cross-linking agent) may be blended.

The light-shielding layer is provided by applying an aqueous suspension of light-shielding particulates containing a hydrophilic polymer binder by means of a known method, and then dried. The volume ratio of light-shielding particulates to hydrophilic polymer binder in the dry state are light-shielding particulates 10: hydrophilic polymer binder about 2.5-about 7.5, preferably about 3.0-about 6.5. In the case that the light-shielding particulates are titanium dioxide particulates, the ratio by weight of polymer binder is about 0.6-about 1.8, preferably about 0.8-about 1.5 per 10 of titanium dioxide. Thickness of the light-shielding layer in dry state is about 3 $\mu$m to about 30 $\mu$m, preferably about 5 $\mu$m to about 20 $\mu$m.

An adhesive layer may be provided in order to adhere a spreading layer, a light-shielding layer, etc. In the case that a porous spreading layer is provided on a light-shielding layer, the adhesive layer is essential. The adhesive layer mainly comprises the hydrophilic polymer binder to adhere the spreading layer at the wetting state or the swelling state of the polymer. The hydrophilic polymer binder usable for the adhesive layer may be selected from the illustrated in the foregoing hydrophilic layer, and gelatin, a gelatin derivative and polyacrylamide are preferable. The thickness of the adhesive layer in dry state is about 0.5 $\mu$m to about 20 $\mu$m, preferably about 1 $\mu$m to about 10 $\mu$m. A surfactant may be added to the adhesive layer. A nonionic surfactant, particularly having a chain structure of 8–15 hydroxyethylene or hydroxypropylene units is preferable.

The adhesive layer may be provided by applying a solution containing the hydrophilic polymer binder and a surfactant added by request by means of a known method.

The integral multilayer analytical element of the invention contains cholesterol esterase, cholesterol oxidase, peroxidase and a coloring reagent composition.

Cholesterol esterase (E.C. 3.1.1.13) catalyzes the conversion of cholesterol esters contained in a sample of cholesterol, and cholesterol oxidase (E.C.1.1.3.6) oxidizes cholesterol to produce hydrogen peroxide. Peroxidase (E.C.1.11.1.7) oxidises 4-aminoantipyrine by utilizing this hydrogen peroxide to couple with 2-hydroxy-3,5-dichlorobenzene sulfonic acid. These enzymes are commercially available, and the enzymes of which the optimum pH and the stable pH are in the range of 7.5 to 9.0 are preferable. However, since the optimum pH of usual enzymes of these are in the range of 6 to 7, the amounts of the enzymes are preferably increased.

As the coloring reagent composition, a combination of 4-aminoantipyrine or its derivative and 2-hydroxy-3,5-dichlorobenzene sulfonic acid is employed. Examples of 4-aminoantipyrine derivative are 1,2,3-tri-substituted 4-amino-3-pyrazoline-5-one as disclosed in GB 2,118,170 B and EP 0,103,901 A and represented by 4-amino-2,3-dimethyl-1-(3-chlorophenyl)-3-pyrazoline-5-one, 4-amino-2,3-dimethyl-1-(2,4,6-trichlorophenyl)-3-pyrazoline-5-one, 4-amino-2-methyl-3-phenyl-1-(2,4,6-trichlorophenyl)-3-pyrazoline-5-one and their salts where an acid is combined with the amino group, such as, hydrochloride. 4-dimethylamino-2,3-dimethyl-1-phenyl-3-pyrazoline-5-one and sodium 1-phenyl-2,3-dimethyl-5-pyrazolone-4-methylaminomethane sulfonate as disclosed in U.S. Pat. No. 3,886,045 are also included. 2-hydroxy-3,5-dichlorobenzene sulfonic acid may be a salt, such as, sodium salt and potassium salt.

Other reagents may be added according to kind of the sample etc. Such reagents include a protein-releasing agent, such as, a nonionic surfactant, as anti-foggant such as dimedone, a sensitivity moderator, and a buffer.

The nonionic surfactant includes a polyhydric alcohol ester ethylene oxide adduct (condensate), a polyethylene glycol monoester, a polyethylene glycol diester, a higher alcohol ethylene oxide adduct (condensate) and an alkylphenol ethylene oxide adduct (condensate). Examples of the nonionic surfactant are disclosed in U.S. Pat. Nos. 3,925,164, 3,983,005, 4,275,152 and 4,275,151, and include, POE (10) sorbitan monooleate
PEG (400) monostearate
Lauryl alcohol EO 10 moles condensate
POE (10) octylphenyl ether
POE (15) octylphenyl ether
POE (12) nonylphenyl ether
Hydroxypolyethoxydodecane
(Note) POE: Polyethylene oxide
PEG: Polyethylene glycol
EO: Ethylene oxide The number in parentheses represents condensation number of ethylene oxide units The enzymes, the coloring reagent composition and other reagents may be contained in one or more layers of the hydrophilic layer, the spreading layer, the reagent layer, etc.

In the multilayer analytical element of the invention, pH of the layer where coloring reaction proceeds is kept in the range of 7.5 to 9, preferably 7.7 to 8.5. In order to adjust to such a pH range, a compound having a buffer action including a phosphate, such as, monosodium dihydrogenphosphate or monopotassium dihydrogen phosphate, a carbonate or a citrate. Since the enzymes, the coloring reagent composition and other reagents migrate according to the spread of the spotted aqueous liquid sample, the layer where the coloring reaction proceeds is not limited to the layer where the reagents are previously added. On the other hand, it is not necessary that all layers where the coloring reaction proceeds is adjusted to such a pH range, and it may be constituted so that pH of the layer where the coloring reaction mainly proceeds, for example the hydrophilic layer, is adjusted to the above range.

The integral multilayer analytical element of the invention is preferably cut into square or circular pieces having a side or diameter of about 15 mm to about 30 mm, and put in a slide frame disclosed in Japanese Patent KOKAI No. 57-63452, U.S. Pat. Nos. 4,169,751, 4,387,990, PCT application WO No. 83/00391, etc. to use.

The sample to be measured in an aqueous liquid containing cholesterol. Such a sample includes a blood sample, such as, whole blood, blood plasma and blood serum, other body fluids, on a sample for process control in a factory which produces or utilizes cholesterol.

The measurement is carried out, for example, according to the manner disclosed in the specifications of the foregoing patents. About 5 $\mu$l to about 30 $\mu$l, preferably about 8 $\mu$l to about 15 $\mu$l of an aqueous sample is spotted on the spreading layer, and incubated at a definite temperature in the range of about 20° C. to about 45° C. for a pescribed time, if necessary. Thereafter, a detectable variation, such as, color change or coloring in the multilayer analytical element is measured from the side of the support through reflection photometry, and the subject component in the sample is determined by the principle of colorimetry.

In the case of the integral multilayer analytical element of the present invention, fogging hardly occurs during preservation, and the analytical element can stably be preserved. Coloring concentration is sufficient, and it corresponds to conventionally analytical element where a leuco pigment was utilized. Accordingly, both its sensitivity and accuracy of measurement are no problem.

EXAMPLES

Example 1

A colorless transparent polyethylene terephthalate (PET) film of which the thickness was 180 $\mu$m and on which gelatin undercoating was provided was employed as the support. On the support, a solution was applied and dried to form the following hydrophilic layer (water absorption layer) of which dry thickness was 20 $\mu$m.

Gelatin; 26 g/m$^2$
Polyoxyethylene nonyl phenyl ether; 0.03 g/m$^2$ (Containing 8-15 hydroxyethylene units)
Bis(vinylsulfonyl methyl)ether; 30 mg/m$^2$ The hydrophilic layer was dampened with 30 g/m$^2$ of water. A PET tricot fabric cloth (knitted from 50 deniers PET spun yarn, being about 250 $\mu$m in mean thickness) treated with glow discharge was pressed to laminate thereon as the spreading layer, and then dried.

Subsequently, an aqueous solution of the reagent composition for the detection of cholesterol having the following composition was applied on the spreading layer, and dried to prepare 10 kinds of an integral multilayer analytical element for the determination of cholesterol.

Methyl cellulose; 3.0 g/m$^2$ (Methoxyl group content; 29%, Viscosity; 112 cps 2 wt.% aqueous solution at 20° C.)
Titanium dioxide particulates; 24 g/m$^2$ (Rutile type, Particls size; 0.25–0.40 $\mu$m)
Cholesterol oxidase; 3500 IU/m$^2$
Cholesterol esterase; 2000 IU/m$^2$
Peroxidase; 2900 IU/m$^2$ Octylphenoxypolyethoxyethanol; 0.7 g/m² (Non-ionic surfactant, Hydroxyethylene units; 9–10)

Sodium 2-hydroxy-3,5-dichlorobenxene; 1.8 g/m² sulfonate 4-aminoantypyrine; 0.3 g/m²

Dimedone [126-81-8]; 50 mg/m²

Sodium dihydrogenphosphate; 4.0 g/m²

5N-NaOH aqueous solution;

The amount of 5N-NaOH is so that when 10 μl of a control serum "Monitrol IX" (pH 7.4, Dade U.S.A.) is spotted on the spreading layer of the complete element, pH of the spreading layer becomes 5.0, 6.0, 6.5, 7.0, 7.5, 8.0, 8.5, 9.0, 9.5 or 10.0.

The element thus obtained was cut into square pieces of 15 mm×15 mm, and each piece was placed in the plastic mount disclosed in Japanes Patent KOKAI No. 57-63452 to form 10 kinds of chemical-analytical slides for cholesterol determination. Each 10 μl of human sera having various cholesterol concentrations which were drawn with heparin was spotted on the spreading layer of each slide, and incubated at 37° C. for 6 minutes. Reflection optical density was measured by using a light of 540 nm from the PET support side. A calibration curve was prepared by using these results and the colesterol concentrations of the same sera separately determined by a conventional analysis of C. C. Allain et al as criteria.

Subsequently, three modified "Monitrol IX", i.e. "Monitrol IX" to which 10 mg/ml of EDTA-2Na, was added, "Monitrol IX" to which 5 mg/dl of ascorbic acid was added and "Monitrol IX" of which pH was adjusted to 4.0 were prepared. Each modified "Monitrol IX" was spotted on each slide of which prescribed pH is different, and incubated to appear a color. Each reflection optical density was measured, and changed to weight by using the above calibration curve. Variation ratios against the value obtained from "Monitrol IX" which was defined as one were calculated, and shown in Table 1.

TABLE 1

| | Prescribed pH of Spreading Layer | EDTA-2 Na 0 mg/ml | EDTA-2 Na 10 mg/ml | Ascorbic Acid 5 mg/dl | pH 4.0 |
|---|---|---|---|---|---|
| Comparative | 5.5 | 1.0 | 0.43 | 0.70 | 0.72 |
| | 6.0 | 1.0 | 0.40 | 0.80 | 0.80 |
| | 6.5 | 1.0 | 0.55 | 0.90 | 0.85 |
| | 7.0 | 1.0 | 0.80 | 0.92 | 0.90 |
| Invention | 7.5 | 1.0 | 0.98 | 0.94 | 0.99 |
| | 8.0 | 1.0 | 1.00 | 0.96 | 1.00 |
| | 8.5 | 1.0 | 1.00 | 0.96 | 0.99 |
| | 9.0 | 1.0 | 1.00 | 0.96 | 1.00 |

In the cases of the slides of pH 9.5 and pH 10.0, the variations of reflection optical density were small, and it was difficult to obtain suitable calibration curves.

Example 2

Prescribed pH value of the spreading layer was set at 7.8, and chemical-analytical slides for cholesterol determination were prepared in the same manner as in Example 1. These slides were preserved at 4° C. under 20% relative humidity for 8 months. Each 10 μl of the undermentioned four kinds of aqueous liquid samples was spotted on each of the slides just after preparation, after 28 days or after 8 months, and incubated at 37° C. for 6 minutes. Reflection optical density was measured by using a light having a central wave length of 540 nm from the PET support side, and the results shown in Table 2 were obtained.

Aqueous solution of 7% human serum albumin (7% HSA) Cholesterol content; 0 mg/dl "Monitrol II" (Control serum, Dade U.S.A.) Cholesterol content; About 100 mg/dl "Monitrol I" (Control serum, Dade U.S.A.) Cholesterol content; About 200 mg/dl "Precilip EL" (Control serum, Boehringer Mannheim West Germany) Cholesterol content; About 360 mg/dl

TABLE 2

| | Relative Optical Density | | |
|---|---|---|---|
| | Just after (Criterion) | After 28 days | After 8 months |
| 7% HSA | 1 | 1.03 | 1.13 |
| Monitorol II | 1 | 1.00 | 1.01 |
| Monitorol I | 1 | 1.01 | 1.00 |
| Precilip EL | 1 | 0.99 | 0.98 |

The above results indicate that the integral multilayer analytical element of the invention is superior for preservation, and degradation during preservation is minor.

We claim:

1. In an integral multilayer analytical element for analysis of cholesterol consisting essentially of a water-impermeable light-transmissive support, a water absorption layer containing a hydrophilic polymer binder and spreading layer containing cholesterol and cholesterol oxidase, superposed in this order, and said analytical element further containing peroxidase and a coloring reagent composition, the improvement which consisting essentially of said coloring reagent composition being a combination of 4-aminoantipyrine, its acid adduct salt, its derivative or its acid adduct salt and 2-hydroxy-3,5-di-chlorobenzene sulfonic acid or a salt thereof, and wherein the pH of the layer where the coloring reaction proceeds is kept in the range of 7.5 to 9.

2. The integral multilayer analytical element of claim 1 wherein said derivative is a member selected from the group consisting of 4-amino-2,3-dimethyl-1-(3-chlorophenyl)-3-pyrazoline-5-one, a salt thereof, 4-amino-2,3-dimethyl-1-(2,4,6-trichlorophneyl)-3-pyrazline-5-one, a salt thereof 4-amino-2-methyl-3-phenyl-1-(2,4,6-trichlorophenyl)-3-pyrazoline-5-one and a salt thereof.

3. The integral multilayer analytical element of claim 1 wherein said spreading layer contains the peroxidase and said coloring reagent composition.

4. The integral multilayer analytical element of claim 1 wherein said pH of the layer where the coloring reaction proceeds is kept in the range 7.7 to 8.5.

5. In an integral multilayer analytical element for analysis of cholesterol consisting essentially of a water-impermeable light-transmissive support, a water absorption layer containing a hydrophilic polymer binder and spreading layer containing cholesterol esterase and cholesterol oxidase, superposed in this order, and said analytical element further containing peroxidase and a coloring reagent composition, the improvement which consisting essentially of said coloring reagent composition being a combination of 4-aminoantipyrine, its acid adduct salt, its derivative or its acid adduct salt and 2-hydroxy-3,5-di-chlorobenzene sulfonic acid or a salt thereof, and wherein the pH of the layer where the coloring reaction proceeds is kept in the range of 7.5 to 9, and wherein a light-shielding layer is provided on said water absorption layer.

* * * * *